(12) United States Patent
Nitzan et al.

(10) Patent No.: US 8,808,370 B2
(45) Date of Patent: Aug. 19, 2014

(54) RECOIL INHIBITOR FOR PROSTHETIC VALVE

(71) Applicant: Edwards Lifesciences Corporation, Irvine, CA (US)

(72) Inventors: Yaacov Nitzan, Kertzeliya (IL); Benjamin Spenser, D.N. Hof HaCarmel (IL); Yaron Keidar, Irvine, CA (US); Tamir S. Levi, Moshav Ein Hamek (IL); Melissa Denton Young, Rochester, MN (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/909,890

(22) Filed: Jun. 4, 2013

(65) Prior Publication Data
US 2013/0274871 A1 Oct. 17, 2013

Related U.S. Application Data

(63) Continuation of application No. 12/202,131, filed on Aug. 29, 2008, now abandoned.

(60) Provisional application No. 60/969,522, filed on Aug. 31, 2007.

(51) Int. Cl.
*A61F 2/06* (2013.01)
*A61F 2/24* (2006.01)
*A61F 2/95* (2013.01)

(52) U.S. Cl.
CPC ............ *A61F 2/2427* (2013.01); *A61F 2/2433* (2013.01); *A61F 2002/9522* (2013.01)
USPC ..................... 623/2.11; 623/1.11; 623/1.12

(58) Field of Classification Search
None
See application file for complete search history.

(56) References Cited

U.S. PATENT DOCUMENTS

| | | | | |
|---|---|---|---|---|
| 6,863,683 | B2 * | 3/2005 | Schwager et al. | 623/1.11 |
| 6,893,460 | B2 * | 5/2005 | Spenser et al. | 623/2.14 |
| 2005/0288764 | A1 * | 12/2005 | Snow et al. | 623/1.11 |
| 2007/0239254 | A1 * | 10/2007 | Chia et al. | 623/1.11 |

* cited by examiner

*Primary Examiner* — Melanie Tyson
*Assistant Examiner* — Todd J Scherbel
(74) *Attorney, Agent, or Firm* — Pui Tong Ho; David L. Hauser

(57) ABSTRACT

A valve loading apparatus is provided for loading a crimped prosthetic valve into a lumen of a delivery system. The valve recoil adapter can counteract recoil of a compressed prosthetic valve, and maintain the valve at its desired crimp diameter. An integrated bioprosthesis/delivery system is provided for delivering a bioprosthesis to a target area within a body lumen is provided. The delivery system includes a valve covering member and a compressing member, which compresses the valve covering member to surround, hold, and/or compress the valve during delivery to the target area.

5 Claims, 10 Drawing Sheets

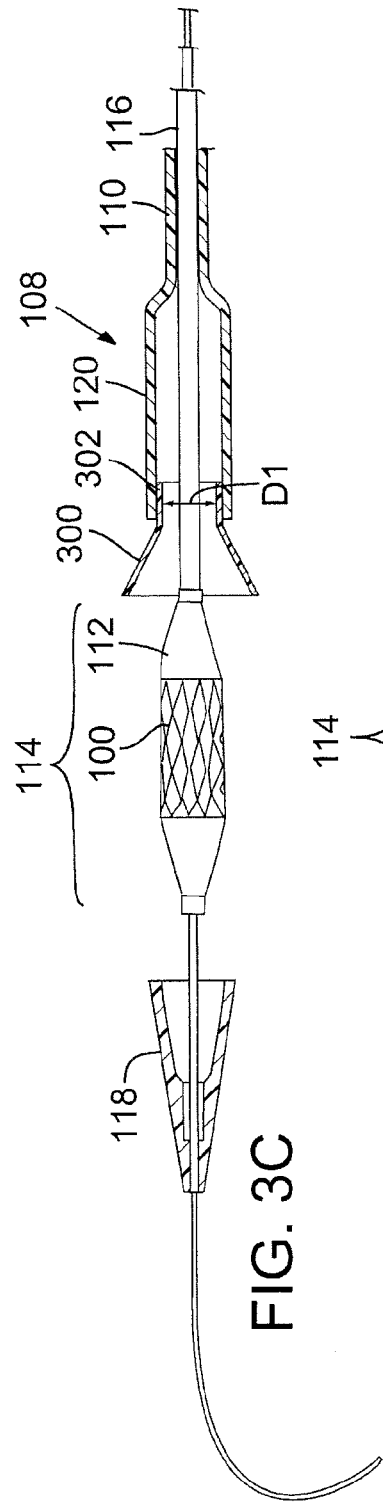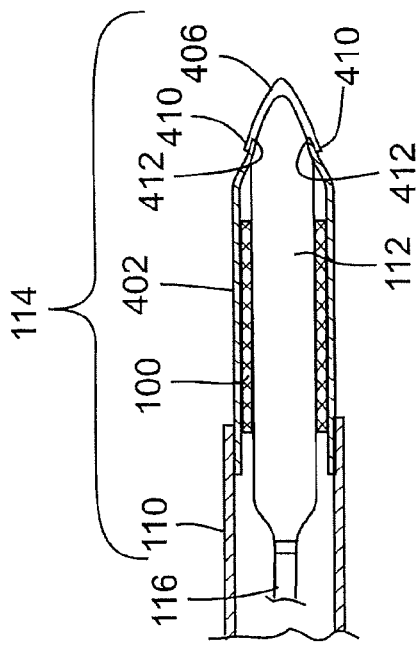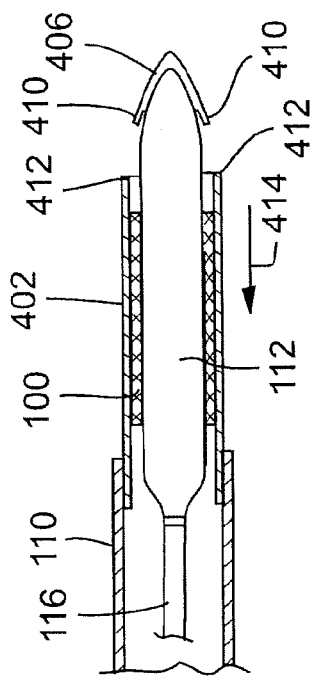
FIG. 3C
FIG. 4A
FIG. 4B

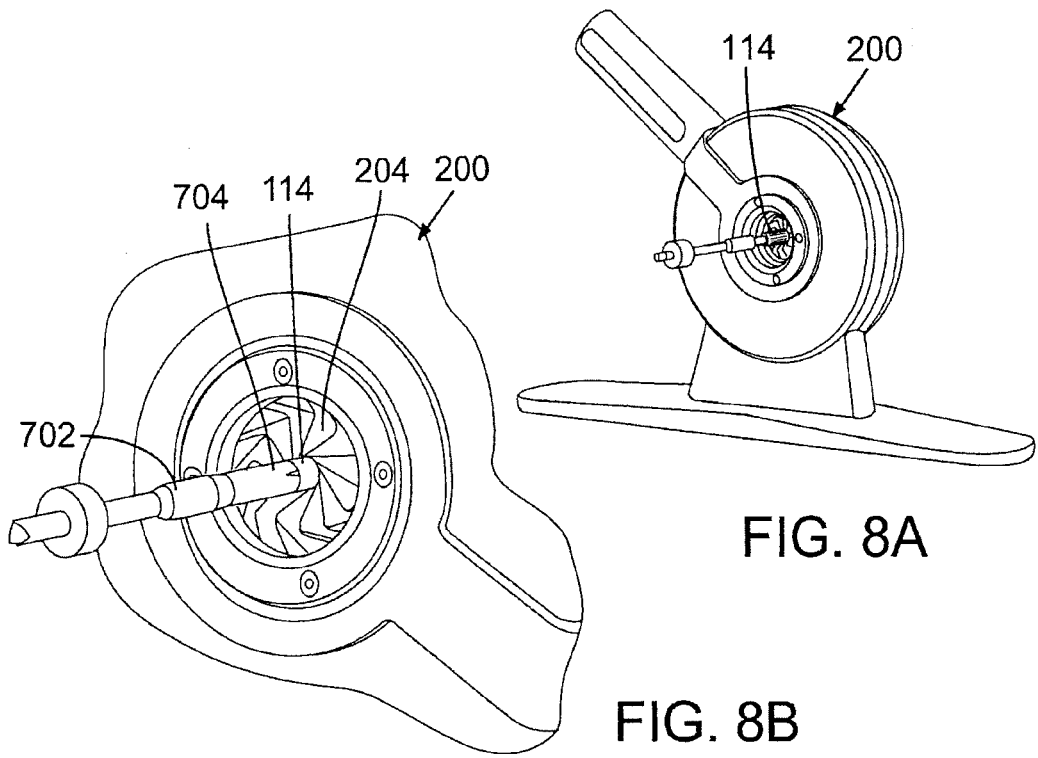
FIG. 8A
FIG. 8B
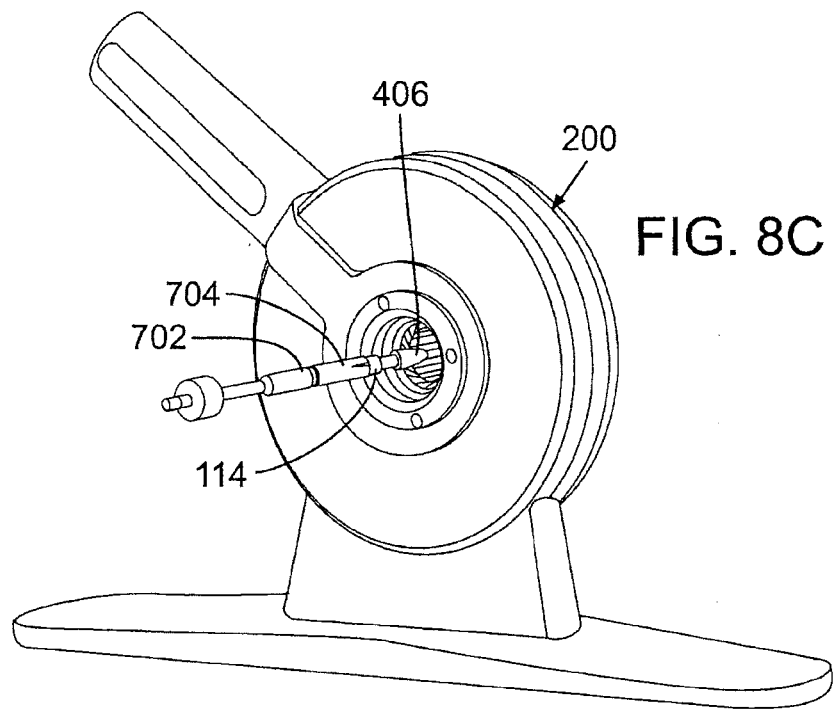
FIG. 8C

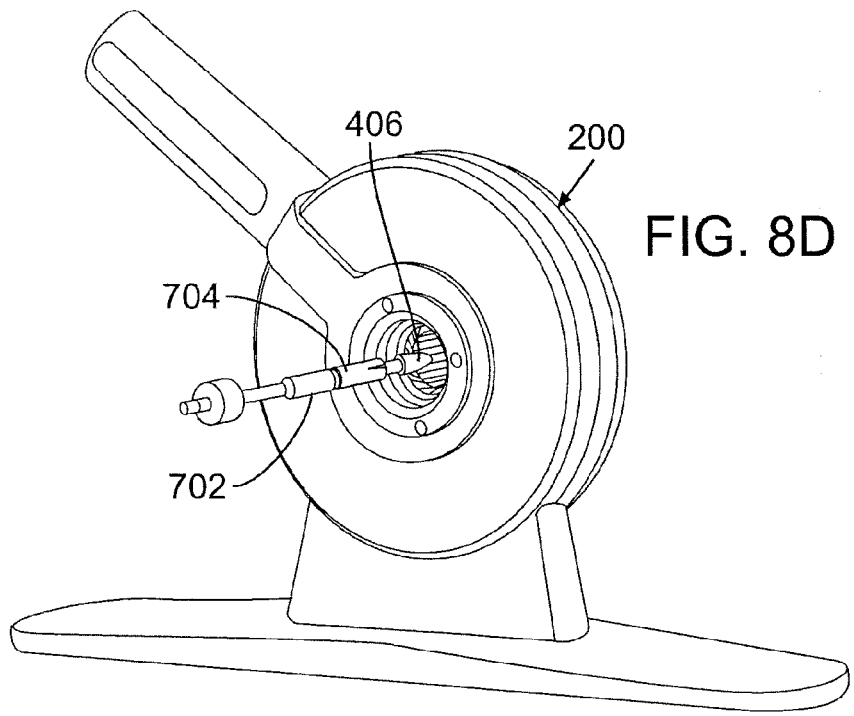
FIG. 8D
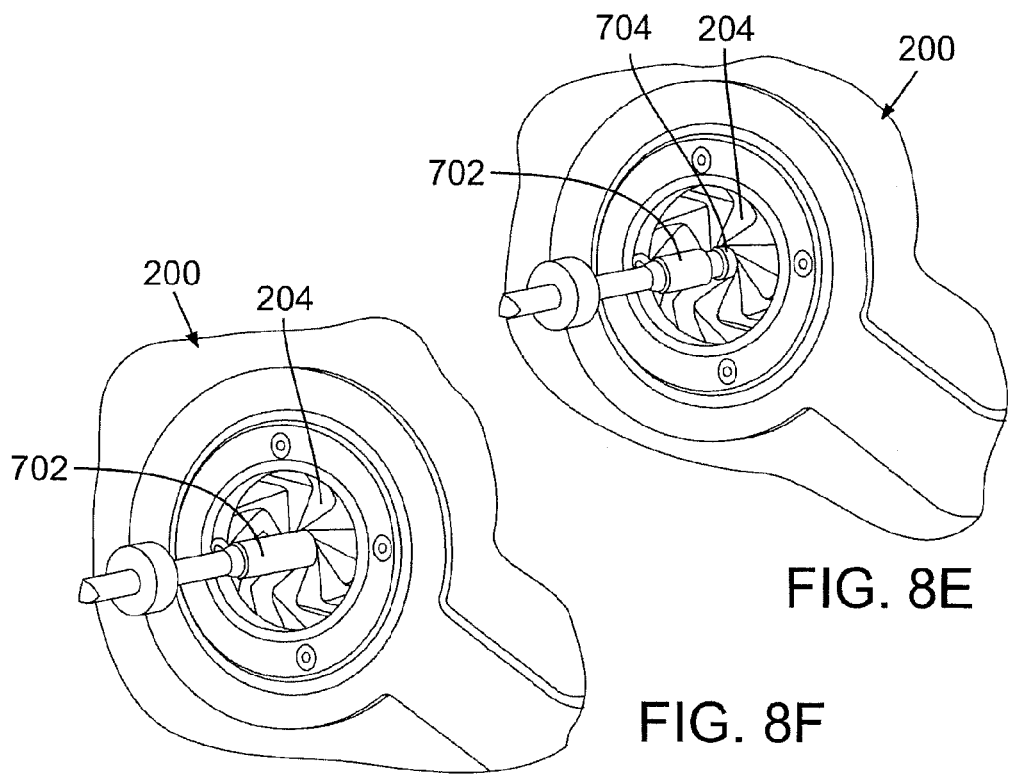
FIG. 8E
FIG. 8F

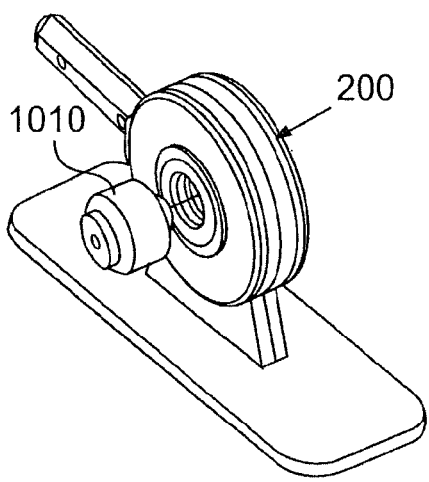
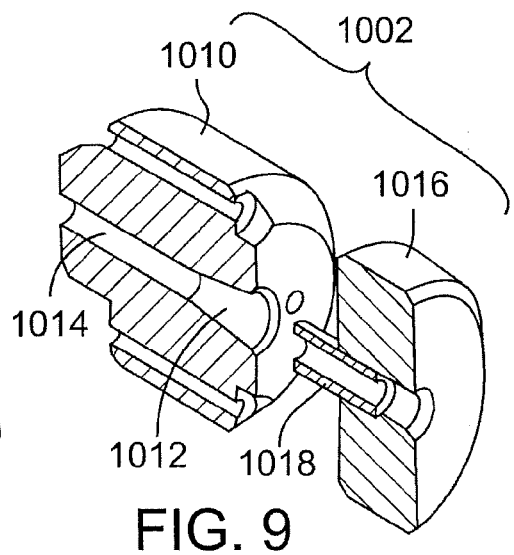
FIG. 10    FIG. 9
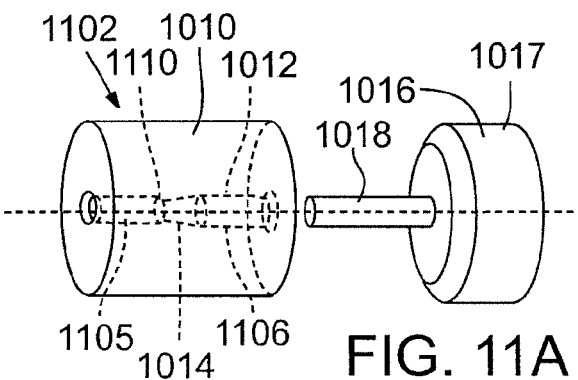
FIG. 11A
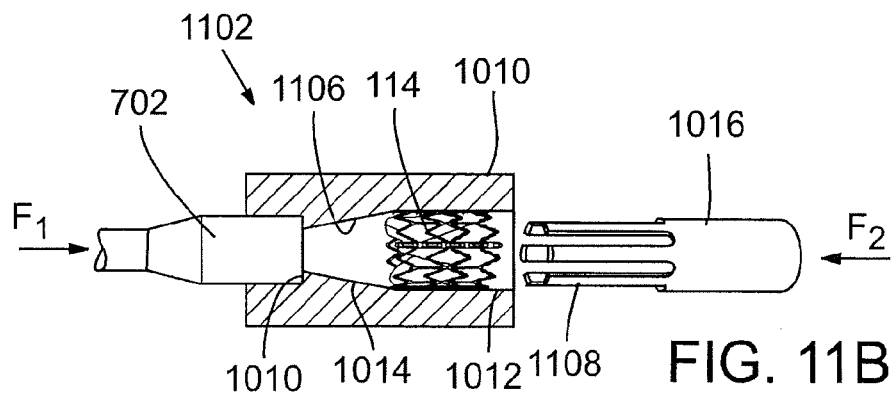
FIG. 11B

RECOIL INHIBITOR FOR PROSTHETIC VALVE

CROSS-REFERENCE TO RELATED APPLICATION

This application is a continuation of U.S. application Ser. No. 12/202,131, filed Aug. 29, 2008, which claims priority to commonly assigned U.S. provisional patent application No. 60/969,522 filed Aug. 31, 2007, which is hereby incorporated by reference in its entirety.

FIELD

The invention relates generally to delivery catheters and, more particularly, to a method and device for preparing a stented prosthetic valve for delivery into a patient's body.

BACKGROUND

A variety of prosthetic valves have been developed for replacing defective native valves, such as an aortic heart valve, in a human body. Prosthetic valves typically include a valve structure mounted on a stent which is delivered to a treatment site via a percutaneous catheterization technique. A stent is a generally cylindrical prosthesis introduced into a lumen of a body vessel via a catheterization technique. Stents may be self-expanding or balloon expandable. Balloon-expandable stents are typically crimped from an initial large diameter to a smaller diameter prior to advancement to a treatment site in the body. Before crimping, a balloon expandable stent is typically placed over an expandable balloon on a catheter shaft.

To properly position a balloon expandable stent on a delivery catheter over the expandable balloon, the stent must be smoothly and evenly crimped to closely conform to the overall profile of the catheter and the unexpanded balloon.

Despite the most careful and firm crimping, physical properties of the material used in manufacturing stents (some stainless steels, tantalum, platinum or platinum alloys, CoCr, MP35N or shape memory alloys such as Nitinol™) allow a certain amount of "recoil" of the stent. That is, the stent tends to slightly open up from its crimped diameter once the crimping force has been removed. In some instances, the stent diameter has been shown to increase about 15% from its crimped diameter.

The enlarged recoil diameter increases the overall profile of the underlying catheter and balloon. Thus, since the stented prosthetic valve is configured to be delivered percutaneously, in a less invasive procedure, a smaller device is beneficial.

SUMMARY

In one embodiment, a valve recoil inhibitor adapter is provided which may be attached onto a loader or delivery system component. The valve recoil adapter counteracts the stent recoil and maintains the overall valve frame and device at its desired crimp diameter.

In another embodiment, a prosthesis assembly, including a bioprosthesis and a balloon catheter, is inserted into or covered with an over tube, which maintains the bioprosthesis in substantially a delivery diameter and prevents the bioprosthesis from recoiling.

In another embodiment, an integrated bioprosthesis/delivery system for delivering a bioprosthesis to a target area within a body lumen is provided. The delivery system includes a moveable cover and a slit tube, where the moveable cover is positioned over the slit tube in a telescoping arrangement. The delivery system encapsulates, holds, and delivers the bioprosthesis to the target area.

In one embodiment, a valve loading apparatus for loading a crimped prosthetic valve into a lumen of a delivery system is provided. The valve loading apparatus comprises a first portion, a second portion, and a transitional portion. The first portion is configured to receive a crimped prosthetic valve. The second portion is configured to be coupled to a distal end of the delivery system. The apparatus has an opening that passes through the first, second, and transitional portions. The opening has a first diameter at the first portion and a second diameter at the second portion, with the first diameter being larger than the second diameter. The transitional portion has a transitional diameter that varies from the first diameter to the second diameter. When the crimped valve is passed through the opening of the loading apparatus and into the lumen of the delivery system, the crimped valve is radially compressed from a larger diameter to a smaller diameter.

In a specific implementation, the second portion has a third diameter section. The third diameter is larger than the second diameter. The transition from the second diameter to the third diameter forms a lip, and the lip is configured to abut the distal end of the delivery system.

In another specific implementation, the valve loading apparatus further comprises a first clamp portion and a second clamp portion, with the first and second clamp portions being separable from one another. The first clamp portion forms a part of each of the first, second, and transitional portions, and the second clamp portion forms the remainder of the first, second, and transitional portions. In another specific implementation, the valve loading apparatus further comprises a pushing member. The pushing member comprises a handle portion and one or more extending portions, with the extending portions having a hollow central area and being sized to extend into the opening of the valve loading apparatus to urge the crimped prosthetic valve through the opening of the valve loading apparatus. In another specific implementation, the extending portions of the pushing member comprise two or more annularly spaced finger members.

In another embodiment, a method of loading a crimped prosthetic valve into a lumen of a delivery system is provided. The method comprises crimping a prosthetic valve on a balloon member of a balloon catheter. The method further comprises providing a loading apparatus, the loading apparatus having a first section and a second section. The first section has a first diameter and the second section has a second diameter. The second diameter is smaller than the first diameter. The method further comprises introducing the crimped prosthetic valve into the first section, wherein at the time of introduction into the first section, the crimped prosthetic valve has a diameter greater than the second diameter. The method further comprises passing the crimped prosthetic valve through the second section and into the lumen of the delivery system. The crimped prosthetic valve exits the second section with the crimped prosthetic valve having a diameter that is equal to or less than the second diameter.

In a specific implementation, the method further comprises coupling the second section of the loading apparatus to a distal end of the delivery system. In another specific implementation, the method further comprises passing the balloon member through an introducer sheath prior to prior to crimping the prosthetic valve on the balloon member. In another specific implementation, the act of passing the crimped prosthetic valve through the second section further comprises providing a pushing member; and using the pushing member to apply a force to the crimped prosthetic valve to push the crimped prosthetic valve through the second section of the loading apparatus.

In another embodiment, an apparatus for delivering a prosthetic valve through the vasculature of a patient is provided. The apparatus comprises a main catheter, a balloon catheter, a valve covering member, and a compressing member. The main catheter comprises a distal section. The balloon catheter comprises an elongated shaft and a balloon member connected to a distal end portion of the shaft, with the balloon member having an external surface configured to receive a crimped prosthetic valve. The valve covering member extends from the distal section of the main catheter and over at least a portion of the balloon member. The valve covering member is compressible to apply a compressive force to the prosthetic valve when the prosthetic is crimped on the balloon member. The compressing member is configured to compress at least a portion of the valve covering member.

In specific implementations, the compressing member comprises a nose piece, the nose piece being disposed distal to the balloon member and being configured to receive at least a portion of a distal end of the valve covering member. In other specific implementations, the nose piece is coupled to a distal end of the balloon member. In other specific implementations, the portion of the distal end of the valve covering member that is received by the nose piece has a smaller inner diameter than a portion of the valve covering member that is not received by the nose piece. In other specific implementations, the portion of the distal end of the valve covering member that is received by the nose piece comprises at least one slit or notch.

In other specific implementations, the compressing member comprises an outer covering member. The outer covering member has an elongated shaft and is movable longitudinally relative to the valve covering member. The outer covering member is configured to have a smaller inner diameter than an outer diameter of the valve covering member, such that when the outer covering member extends over the valve covering member, the valve covering member is compressed to a smaller inner diameter. In other specific implementations, the valve covering member is adhered to the distal section of the elongated shaft of the main catheter. In other specific implementations, the valve covering member is integrally formed with the distal section of the elongated shaft of the main catheter.

In another embodiment, a method of loading a crimped prosthetic valve into a lumen of a delivery system is provided. The method comprises providing a main catheter with an elongated shaft; providing a balloon catheter with an elongated shaft and a balloon member disposed at a distal end of the elongated shaft; crimping a prosthetic valve on the balloon member; providing a valve covering member, the valve covering member being configured to extend at least from a distal end of the main catheter to a distal end of the balloon member, the valve covering member having at least one slit or notch at a distal portion of the valve covering member; covering the crimped prosthetic valve with the valve covering member; crimping at least a portion of the valve covering member to a smaller profile, the portion of the valve covering member that is crimped covering at least a portion of the crimped prosthetic valve during the act of crimping; providing an outer covering member, the outer covering member having an elongated shaft; and moving the outer covering member to extend over the portion of the valve covering member that covers the crimped prosthetic valve, the outer covering member being sized to apply a compressive force to the valve covering member. In specific implementations, at least a part of the act of moving the outer covering member over the valve covering member occurs while the valve covering member is loaded into a crimping device.

The foregoing and other features and advantages of the invention will become more apparent from the following detailed description, which proceeds with reference to the accompanying figures.

BRIEF DESCRIPTION OF THE DRAWINGS

FIGS. 3B and 3C are exemplary illustrations of a valve recoil inhibitor positioned on a delivery system in accordance with an embodiment disclosed herein.

FIGS. 4A and 4B are illustrations of an embodiment disclosed herein.

FIGS. 8A-8G show an exemplary process for loading a prosthesis assembly into delivery system in accordance with an embodiment disclosed herein.

FIG. 9 is an illustration of a loading tool in accordance with an embodiment disclosed herein.

FIG. 10 is an illustration of a loading tool in accordance with an embodiment disclosed herein.

FIG. 11A is an illustration of a loading tool in accordance with an embodiment disclosed herein.

FIG. 11B is an illustration of a loading tool and an integrated bioprosthesis/delivery system in accordance with an embodiment disclosed herein.

DETAILED DESCRIPTION

The following description is exemplary in nature and is not intended to limit the scope, applicability, or configuration of the invention in any way. Various changes to the described embodiment may be made in the function and arrangement of the elements described herein without departing from the scope of the invention.

Figure 1A:
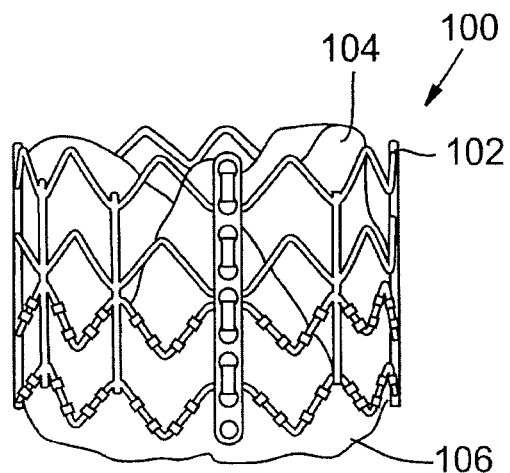
FIG. 1A illustrates an exemplary embodiment of a balloon expandable prosthetic heart valve.

FIG. 1A illustrates an exemplary embodiment of a balloon expandable prosthetic heart valve 100 (hereinafter, "bioprosthesis 100"). Bioprosthesis 100 includes an implantable structure 102 (also referred to herein as a stent or support frame), a flexible membrane 104, and a membrane support 106. Implantable structure 102 is expandable from a first reduced diameter to a second enlarged diameter, and has a flow path along a longitudinal axis. Implantable structure 102 generally may be a tubular framework, such as a stent as shown in the illustrated example, which primarily anchors bioprosthesis 100 within or adjacent the annulus of the defective valve in the heart. Implantable structure 102 provides stability and helps prevent bioprosthesis 100 from migrating after it has been implanted.

Flexible membrane 104 is positionable in the flow path for permitting flow in a first direction, and substantially resisting flow in a second direction. In one preferred configuration, the flexible membrane can be formed from tissue, such as, for example, bovine pericardial tissue, or a suitable biocompatible, synthetic material such as those described in U.S. Pat. No. 6,730,118, which is incorporated herein by reference. Membrane support 106 is positionable in the flow path and affixed, such as by suture, to implantable structure 102. Membrane support 106 can comprise a fabric skirt that surrounds the lower portion of the membrane 104 to reinforce the connection between the membrane 104 and the frame 102.

Figure 1B:
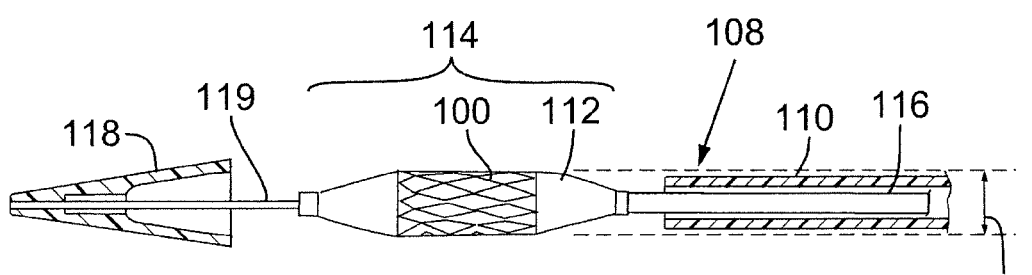
FIG. 1B is a simplified side view of a balloon expandable prosthetic heart valve delivery system that is configured to support and deliver the balloon expandable prosthetic heart valve in FIG. 1A to a target area inside a patient's body.

Prior to implantation, bioprosthesis 100 is carefully mounted and crimped onto a catheter assembly (delivery assembly) 108 (hereinafter, "assembly 108"), which can include a delivery catheter 110 and a balloon catheter with an elongated shaft 116 and a balloon member 112 (FIG. 1B). The balloon catheter can have an inner lumen that is in fluid communication with the balloon member 112 and a fluid pressurizing device (not shown). During inflation of the balloon member 112, fluid passes from the fluid pressurizing device to the balloon member 112 and the balloon member is inflated with a controlled volume of fluid (e.g., saline/contrast).

Delivery catheter 110 can be used to deliver and deploy the appropriate size bioprosthesis 100. Delivery catheter 110 can be a guide catheter or flex catheter that is configured to be selectively steerable or bendable to assist the surgeon in guiding the delivery assembly 108 through the patient's vasculature. In one embodiment, delivery catheter 110 advances bioprosthesis 100 through a sheath over a guidewire and tracks bioprosthesis 100 through the aortic arch. Delivery catheter 110 also aids in crossing, and positioning bioprosthesis 100 within the native valve. Delivery catheter 110 can include a tapered nose cone 118 mounted at the distal end of a respective catheter shaft 119, which allows assembly 108 to cross the native valve easily. In one exemplary operation, bioprosthesis 100 and assembly 108 are inserted into the femoral artery and delivered to the site of the native stenotic aortic valve. Bioprosthesis 100 is positioned and deployed across the stenotic native valve. The balloon delivery system is then removed. An exemplary bioprosthesis 100 designed for transfemoral implantation in patients with severe aortic stenosis (AS) is the SAPIEN transcatheter heart valve model 9000TFX available from Edwards Lifesciences Corporation, Irvine, Calif., the assignee of the present invention. An exemplary catheter assembly 108 designed to deliver bioprosthesis 100 is the RETROFLEX II catheter assembly also available from Edwards Lifesciences Corporation, Irvine, Calif. The bioprosthesis can be implanted in a retrograde approach where the bioprosthesis, mounted in a crimped state at the distal end of a delivery apparatus, is introduced into the body via the femoral artery and advanced through the aortic arch to the heart, as further described in U.S. Patent Publication No. 2008/0065011, which is incorporated herein by reference.

Although the operation described above is a performed with an elongate catheter in a percutaneous transfemoral procedure, it should be understood that the present invention may also be used with a shorter catheter assembly in a minimally-invasive surgical transapical procedure for treating a defective aortic valve. In the transapical procedure, the bioprosthesis is preferably advanced into the heart through a small incision formed between two ribs and through an incision formed in the apex of the heart. Although the transapical procedure is generally considered a more invasive approach as compared with the percutaneous transfemoral procedure, the direct line of access used in the transapical procedure provides the physician with greater degree of control during advancement and deployment of the bioprosthesis.

Figure 2:
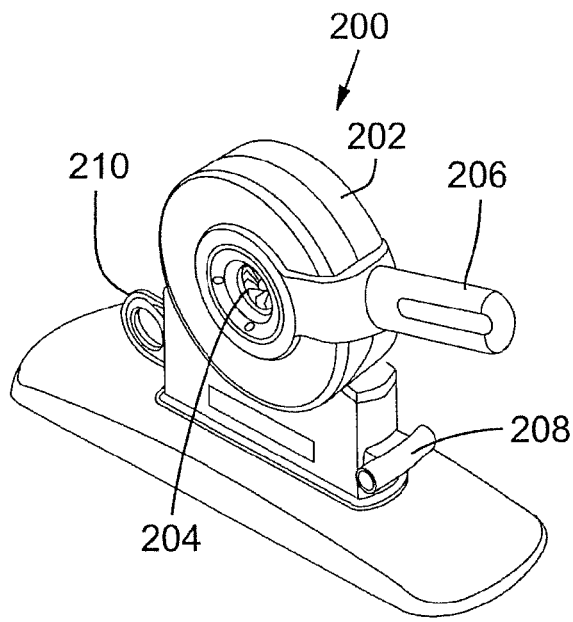
FIG. 2 is an illustration of a crimping device used to mount a bioprosthesis to a balloon catheter.

With reference now to FIG. 2, a crimping device 200 is illustrated which may be used to mount bioprosthesis 100 to the catheter assembly 108. In one embodiment, crimping device 200 is a single-use non-patient contacting, compression device that symmetrically reduces the overall diameter of bioprosthesis 100 from its expanded size to its collapsed (mounted) size, effectively mounting bioprosthesis 100 to its delivery balloon catheter 112. Crimping device 200 includes a housing 202 and a compression mechanism 204. Compression mechanism 204 is closed by means of a handle 206 located on housing 202. Crimping device 200 is also equipped with two measuring gauges: a crimp gauge 208 to verify that the bioprosthesis/balloon assembly has been suitably collapsed, and a balloon gauge 210 to verify the bioprosthesis/balloon assembly catheter diameter when inflated. Further details relating to a crimping device can be found in U.S. Patent Publication No. 2007/0056346, which is incorporated herein by reference.

As mentioned above, despite the most careful and firm crimping of bioprosthesis 100 and balloon catheter 112 to closely conform to the overall desired profile of the catheter unexpanded balloon 112 and underlying inflatable tube components, there is a certain amount of "recoil" of implantable structure 102 (hereinafter, "stent 102") or a tendency of stent 102 to slightly open from a desired hypothetical minimum crimped diameter. This tendency of stent 102 to open or recoil slightly when crimped on balloon catheter 112 has been characterized as "recoil." The actual minimum diameter achievable for fully crimped stent 102 on balloon catheter 112 is referred to as delivery diameter D1 (FIG. 1B).

Figure 3A:
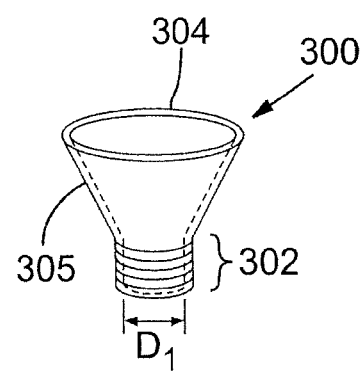
FIG. 3A is a illustration of a valve recoil inhibitor in accordance with an embodiment disclosed herein.
Figure 3B:
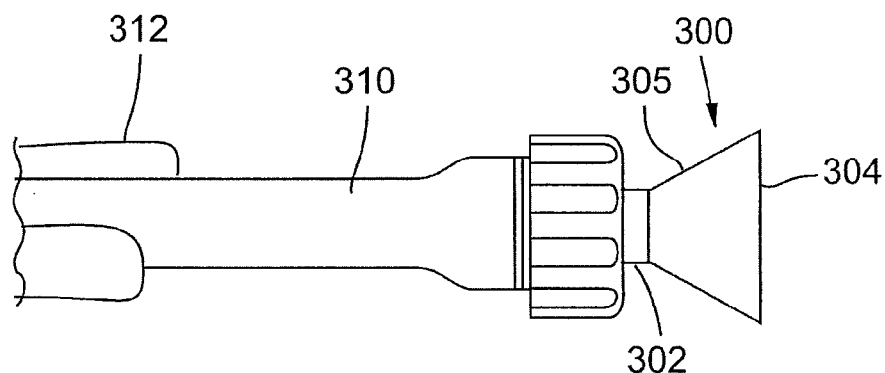

In a first embodiment shown in FIGS. 3A-3C, a valve recoil adapter 300 is illustrated which may be used to counteract stent recoil by compressing a crimped valve to the delivery diameter D1 of bioprosthesis 100 as it is inserted into a delivery device. Valve recoil adapter 300 includes a first portion with a large open end 304 and second portion with a crimp diameter portion 302. A frusto-conical transitional portion 305 extends between the first and second portions. Crimp diameter portion 302 may be variably sized to any desired delivery diameter.

In operation, as shown in FIGS. 3A, 3B and 3C, after crimping bioprosthesis 100 onto balloon catheter 112 to form a prosthesis assembly 114 (using, for example, crimping device 200), prosthesis assembly 114 is inserted into large open end 304 of valve recoil adapter 300 until it can be force fit into crimp diameter portion 302. The crimp diameter portion 302 counter acts any recoil that stent 102 on prosthesis assembly 114 has experienced after crimping by radially compressing prosthesis assembly 114 back to its desired delivery diameter D1. In the absence of valve recoil adapter 300, the delivery diameter D1 is dependent on random recoil that the material experiences after the crimping process. Valve recoil adapter 300 allows the practitioner to control the delivery diameter D1 of prosthesis assembly 114.

Referring to FIG. 3B, in one embodiment, valve recoil adapter 300 can be configured for use with another delivery system, i.e., loader device 310. For the purposes of this application, the term "delivery system" refers to any apparatus or structure that has a lumen or other opening into which a prosthesis assembly can be received and includes, for example, a catheter, a loader device, and an introducer sheath. Loader device 310 has a lumen into which a prosthesis assembly can be loaded. Loader device 310 can be attached to an introducer sheath (not shown) by clips 312. The distal end of the introducer sheath is inserted into a patient's vessel (e.g., the femoral artery) over a guide wire and receives a delivery assembly, which is inserted through the introducer sheath and into the vessel, as known in the art. Valve recoil adapter 300 is desirably configured to extend into the lumen of the loader device 310 and attach to a proximal end of loader device 310. The method of attachment could include, for example, screwing threaded portions together, clipping, snap fit, etc. Typically, the introducer sheath is long enough to extend through the portion of the delivery path having the smallest diameter. As the prosthesis assembly 114 is inserted through the recoil adapter 300, it is compressed to diameter D1 for insertion through the loader 310 and introducer sheath. Accordingly, the overall cross-sectional profile of the introducer sheath can be reduced to minimize trauma to the patient.

Referring to FIG. 3C, in another embodiment, valve recoil adapter 300 can be configured for use with a delivery catheter 110. Delivery catheter 110 can be configured to receive the prosthesis assembly 114 within an enlarged portion 120 of catheter 110. Valve recoil adapter 300 can be secured to enlarged portion 120 between the prosthesis assembly 114 and the enlarged portion 120. Portion 302 desirably extends into enlarged portion 120. If desired, portion 302 can be secured to the enlarged portion 120 by configuring the recoil adapter 300 and enlarged portion 120 with mating threaded portions or sizing portion 302 so it fits tightly into the enlarged portion 120.

After the valve 100 is crimped onto balloon member 112, the prosthesis assembly 114 is moved longitudinally relative to the delivery catheter 110, such as by retracting shaft 116, to position the prosthesis assembly 114 within the enlarged portion 120. Since valve recoil adapter 300 is positioned between the prosthesis assembly 114 and the enlarged portion 120, the prosthesis assembly 114 must pass through valve recoil adapter 300 before entering the enlarged portion 120 of the delivery catheter 110. As the prosthesis assembly 114 passes through the crimp diameter portion 302, the outer diameter of crimped valve 100 is maintained at (or reduced to) the inner diameter of the crimp diameter portion 302. Once the prosthesis assembly 114 is positioned within the enlarged portion 120, the valve recoil adapter 300 is removed from the assembly. If desired, nose cone 118 can have a hollow section which can be moved proximally to cover the distal end portion of the balloon member 112 and/or valve 100.

If it is desirable to remove the valve recoil adapter 300 from the delivery assembly, such as in the embodiment shown in FIG. 3C, it may be desirable to form the valve recoil adapter in two or more pieces. For example, valve recoil adapter 300 can be formed so that it is split in half longitudinally, with those two halves being configured to fit together to form a single part. The two (or more) parts can attach to one another by various mechanical means, such as by a snap-fit connection. Alternatively, valve recoil adapter 300 can form its cone (or funnel) shape by having a single piece of material that is rolled up into a cone shape. Thus, upon unraveling, the valve recoil adapter 300 can be removed from the assembly.

Referring now to FIGS. 4A-B, in a second embodiment the elongated shaft 116 of the balloon catheter may be inserted through an elongated shaft of catheter 110 with tip mobility, such as Edwards' RETROFLEX II catheter available from Edwards Lifesciences Corporation. Bioprosthesis 100 may be crimped on balloon member 112 using crimping device 200 (FIG. 2) to form prosthesis assembly 114 having, for example, a delivery diameter D1 (FIG. 1B).

As shown in FIG. 4A, prosthesis assembly 114 can be inserted or covered with over tube 402, which substantially maintains prosthesis assembly 114 at delivery diameter D1 and prevents stent 102 from recoiling. Another function of over tube 402 is to provide protection to the blood vessel from the bare stent of bioprosthesis 100.

Over tube 402 can be secured at its proximal end to the inner surface of delivery catheter 110. At its distal end, over tube 402 can be temporarily attached to a tip 406. Tip 406 also can be mounted on (or otherwise attached to) a distal end of balloon member 112. Alternatively, tip 406 can have a separate elongated shaft and can be moveable in the longitudinal direction independently of the elongated shaft of the balloon member.

Tip 406 can have a smaller diameter than the diameter of the elongated shaft of the delivery catheter 110. In addition, tip 406 can have extending portions 410, which are configured to capture and hold a distal portion 412 of over tube 402. Over tube 402 is desirably formed of a material that can be compressed to a smaller diameter at its distal end, so that the distal portion 412 can be inserted and held within the extending portions 410. Accordingly, as shown in FIG. 4A, when the distal portion 412 of over tube 402 is secured at a smaller diameter by tip 406, an inward pressure (a compressive force) is applied by the over tube 402 to prosthesis assembly 114, which reduces and/or maintains the diameter of the prosthesis assembly at the desired delivery diameter.

When the prosthesis assembly 114 is in position for deployment at the treatment site, over tube 402 can be moved proximally and the prosthesis assembly 114 can be uncovered. As shown in FIG. 4B, by moving the shaft of the delivery catheter 110 in the proximal direction, as shown by arrow 414, distal portions 412 of over tube 402 are no longer captured by extending portions 410, and over tube 402 returns to its natural (uncompressed) diameter. Once over tube 402 returns to its natural diameter, prosthesis assembly 114 can be fully uncovered by continuing to move the shaft of the delivery catheter 110 in the proximal direction.

In another embodiment, shown in FIGS. 5A-5D, the distal portion 412 of over tube 402 can be formed with slits (or cuts) 404. Slits 404 permit the over tube 402 to form a tapered portion 408 that extends into and is captured by tip 406. The tapered portion 408 can extend approximately from bioprosthesis 100 to tip 406 of balloon catheter 112.

Figure 5A:
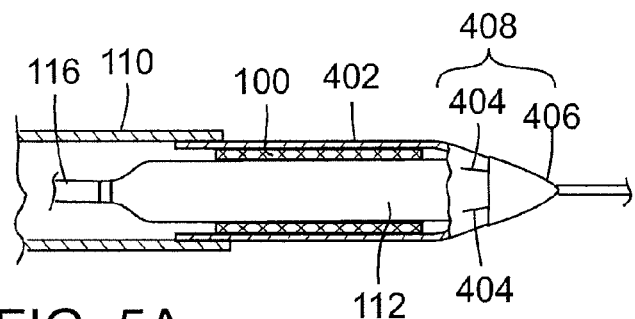
FIGS. 5A-5D are illustrations of an embodiment disclosed herein.

FIG. 5A shows the prosthesis assembly 114 positioned within over tube 402. Distal portion 412 of over tube 402 is positioned so that at least a portion of it is captured within tip 406, causing over tube 402 to be radially compressed and to have a diameter that is smaller than its natural, uncompressed diameter.

Figure 5B:
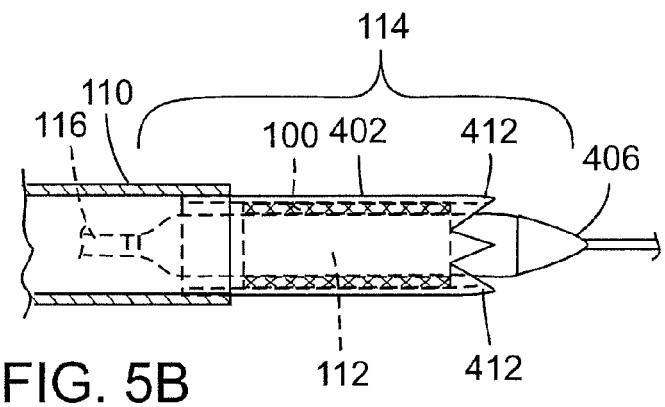

Referring now to FIG. 5B, over tube 402 can be attached to the elongated shaft of delivery catheter 110. Over tube 402 can be attached in a variety of manners to the distal end of the elongated shaft of delivery catheter 110. For example, over tube 402 can be attached to an inner surface of the distal end of the elongated shaft of the delivery catheter 110 (as shown in FIG. 5A) or it can be attached to an outer surface of the elongated shaft of the delivery catheter 110. Over tube 402 can be moved back (proximally) relative to prosthesis assembly 114 by moving the elongated shaft of the delivery catheter 110 (to which over tube 402 is attached) proximal relative to the prosthesis assembly 114. When over tube 402 is pulled back, the distal portion 412 of the over tube 402 is released from the tip 406 and the distal portion 412 of over tube 402 expands to its natural, uncompressed diameter.

Figure 5C:
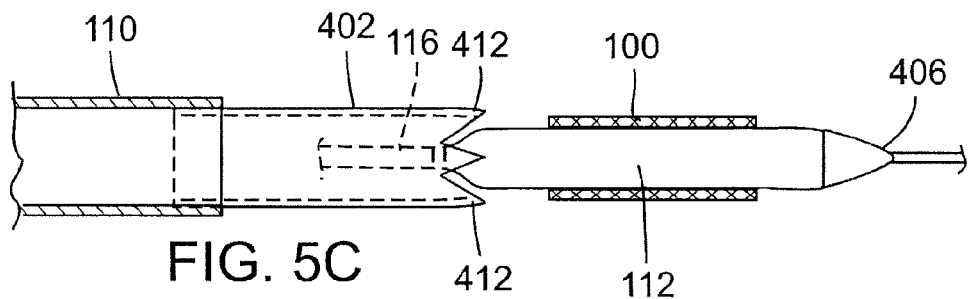
Figure 5D:
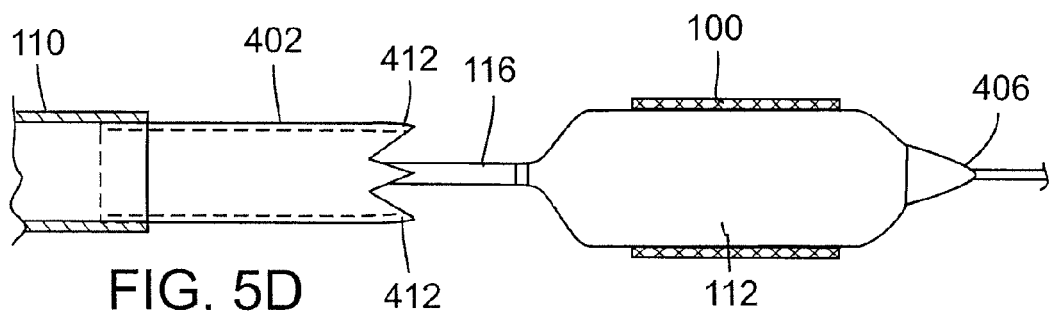

Slits 404 allow over tube 402 to flare open and allows an easy extraction of prosthesis assembly 114 with substantially no friction. Slits 404 can be of any desired length. In addition, as shown in FIG. 5B, slits 404 can be formed as triangular cuts in the distal portion 412 of over tube 402. By forming the slits 404 as triangular cuts, the distal portion 412 can be more easily reduced to a smaller diameter when captured by the tip 406. As shown in FIGS. 5C and 5D, over tube 402 can be pulled back further so that prosthesis assembly 114 is completely exposed, and balloon member 112 may be then inflated freely.

Figure 6:
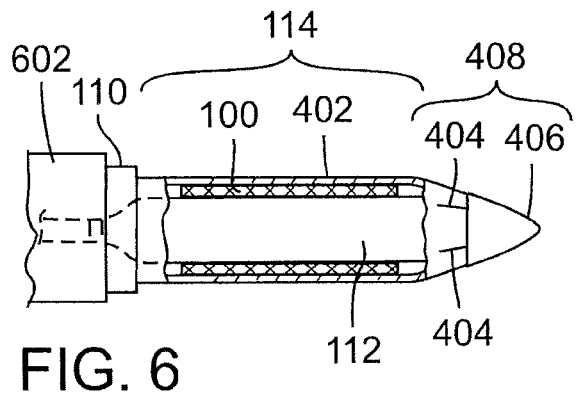
FIG. 6 is a illustration of an embodiment disclosed herein.

In an alternative embodiment, shown in FIG. 6, before crimping bioprosthesis 100 onto balloon member 112, balloon member 112 can be passed through an introducer sheath 602 having a relatively small diameter. As discussed above, introducer sheaths typically extend into the smallest portion of the patient's vasculature. Accordingly, it can be desirable to crimp bioprosthesis after passing it through the introducer sheath. Once bioprosthesis 100 is mounted onto balloon catheter 112 to form prosthesis assembly 114, over tube 402 can be placed over prosthesis assembly 114.

In this embodiment, prosthesis assembly 114 with over tube 402 is loaded in front of introducer sheath 602. Since over tube 402 is relatively thin when compared to the thickness of introducer sheath 602, the total size of the delivery diameter is reduced. Tapered portion 408 can have a smooth, bullet like shape, allows prosthesis assembly 114 to be atraumatically advanced to the heart valve and passed through the calcified valve.

Over tube 402 may be formed from any suitable materials, such as plastics and metals, such as Nitinol and stainless steel. Over tube 402 can be secured to the distal end of the shaft of the delivery catheter by a variety of methods. For example, over tube 402 can be secured on the inside or outside surface of the shaft of the delivery catheter. Alternatively, over tube 402 can extend longitudinally with the delivery catheter 110 (either inside or outside the shaft of the delivery catheter) and can be capable of independent longitudinal movement relative to the shaft of the delivery catheter 110.

Figure 7A:
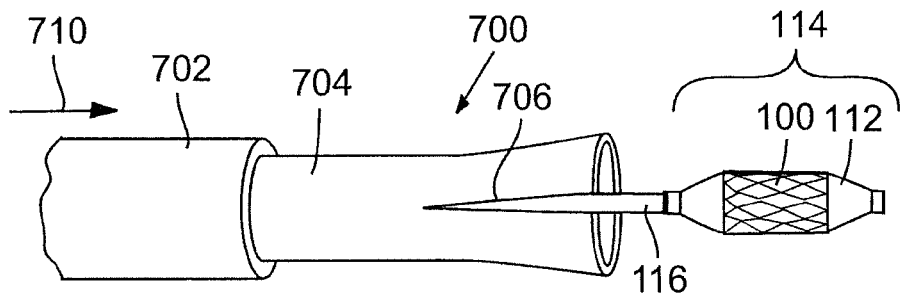
FIGS. 7A and 7B are side views of an integrated bioprosthesis/delivery system loading system in accordance with an embodiment disclosed herein.
Figure 7B:
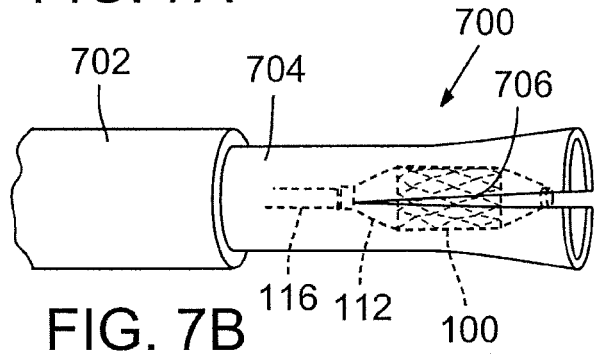

FIGS. 7A and 7B illustrate another embodiment of an integrated bioprosthesis/delivery system 700. In one configuration, delivery system 700 includes a moveable cover 702 and a slit tube 704 in a first or open position. Moveable cover 702 is positioned over slit tube 704 in a telescoping arrangement. Slit tube 704 is disposed at least partially within cover 702 and is longitudinally moveable relative to cover 702. Slit tube 704 includes at least one slit 706, and defines a tubular space sized to receive prosthesis assembly 114, including bioprosthesis 100 and balloon catheter 112.

In operation, prosthesis assembly 114 is positioned within slit tube 704, while moveable cover 702 is in the retracted position (FIG. 7A). Moveable cover 702 is sized so that sliding moveable cover 702 over slit tube 704 in the distal direction (as shown by arrow 710) applies a compression force on prosthesis assembly 114. In this manner, prosthesis assembly 114 is surrounded and squeezed by slit tube 704 and moveable cover 702 so that the entire device has a small profile and is ready for insertion into a body lumen. Sliding moveable cover 702 back relative to slit tube 704 (in the direction opposite arrow 710) allows slit tube 704 to open and release the compression force from prosthesis assembly 114.

Figure 7C:
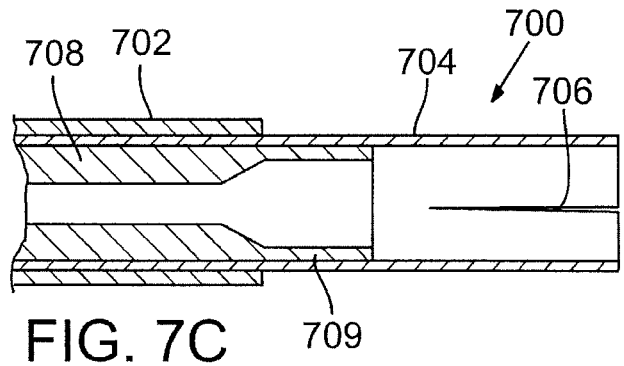
FIG. 7C is a cross sectional view of the integrated bioprosthesis/delivery system loading system of FIG. 7A in accordance with an embodiment disclosed herein.

FIG. 7C is a cross-sectional view of delivery system 700 showing an elongated shaft 708 (e.g., a shaft of a flex or guide catheter) positioned within slit tube 704. Elongated shaft 708 can be formed with an enlarged section 709 that is configured to receive a portion of the prosthesis assembly 114 when it is pulled back into slit tube 704. For clarity, FIG. 7C is shown in partial cross section with the prosthesis assembly 114 removed. Operationally, as moveable cover 702 is moved forward (distally) relative to slit tube 704, cover 702 slides over slit tube 704 and shaft 708, and compresses both slit tube 704 and shaft 708. As shaft 708 is compressed, it captures and holds prosthesis assembly 114 during delivery of prosthesis assembly 114 through the patient's vasculature. Slit tube 704 is desirably adhered to shaft 708, using an adhesive or other securing means.

Slit tube 704 can extend longitudinally to an area just proximal to the distal end of the elongated shaft 708. An inner surface of slit tube 704 can be adhered to an external surface of elongated shaft 708. In such a configuration, movement of elongated shaft 708 effects movement of slit tube 704, and slit tube 704 can be positioned by moving elongated shaft 708. Alternatively, slit tube 704 can extend substantially the length of elongated shaft 708 and can be moveable relative to (and independent of) elongated shaft 708.

Figure 8G:
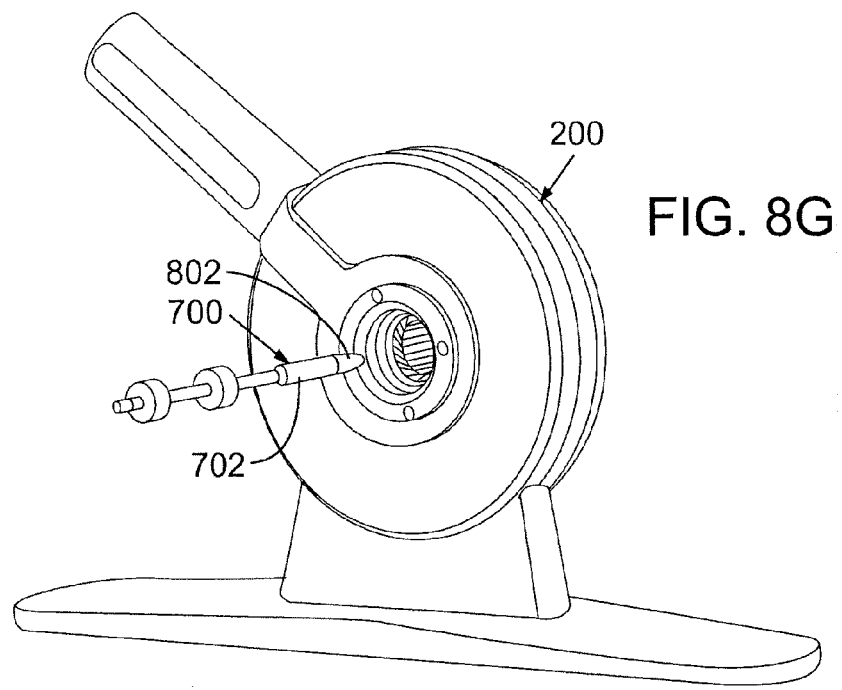

FIGS. 8A-8H show an exemplary process for loading prosthesis assembly 114 into delivery system 700. As shown in FIG. 8A, bioprosthesis 100 and balloon 112 are positioned in crimper 200. Next, bioprosthesis 100 is crimped over balloon catheter 112, forming prosthesis assembly 114 (FIG. 8B). Crimper 200 can be opened and prosthesis assembly 114 can be placed into slit tube 704 by sliding slit tube 704 over prosthesis assembly 114. The slits 706 formed in slit tube 704 permit slit tube 704 to expand (flare out) at its distal end when outward pressure is applied to the area of slit tube 704 near slits 706. FIG. 8C shows slit tube 704 partially covering prosthesis assembly 114 and FIG. 8D shows slit tube 704 completely covering prosthesis assembly 114.

Slit tube 704, including prosthesis assembly 114 positioned therein, can be placed back into crimper 200 and the prosthesis assembly 114 can be crimped again, this time inside of slit tube 704 (FIG. 8E). With the prosthesis assembly 114 and a portion of the slit tube 704 still in the crimper 200, moveable cover 702 can be slid forward over a protruding part of slit tube 704 (FIG. 8F). Crimper 200 can be opened and moveable cover 702 can be slid forward over the remainder of slit tube 704 until moveable cover 702 reaches nose tip 802. By partially extending moveable cover 702 over slit tube 704 prior to releasing slit tube 704 from the crimper 200, moveable cover 702 can resist recoil of the crimped valve 100, at least to the extent that moveable cover 702 extends over a portion of the crimped valve 100. By moving the moveable cover 702 completely over the slit tube 704, moveable cover 702 exerts compressive forces against slit tube 704 and keeps slit tube 704 closed over prosthesis assembly 114 (FIG. 8G).

Figure 8H:
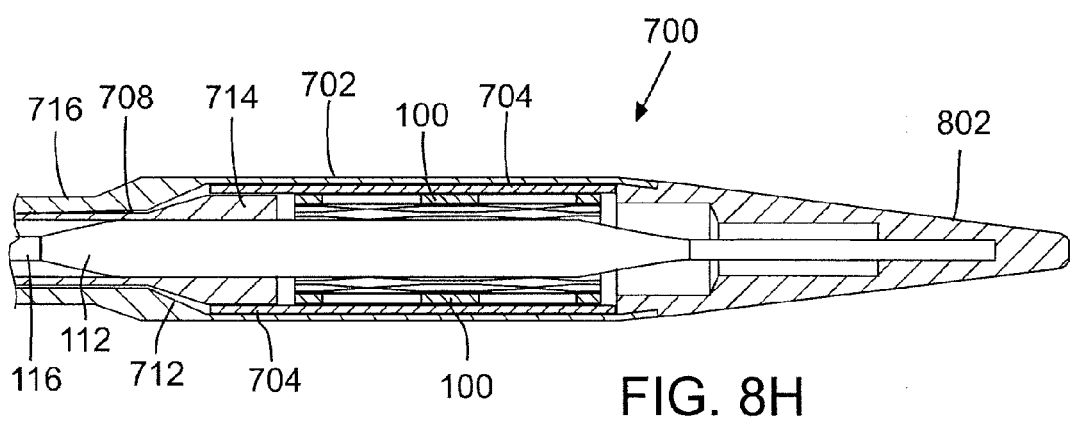
FIG. 8H is a cross sectional view of an integrated bioprosthesis/delivery system in accordance with an embodiment disclosed herein.

FIG. 8H is a cross sectional view of an exemplary delivery system 700 including prosthesis assembly 114 in accordance with an embodiment. Cover 702 abuts nose tip 804 at its distal end and. At its proximal end, cover 702 has a transition portion 712, where the diameter of cover 702 is reduced until it reaches a smaller diameter portion 716. Slit tube 704 extends from a distal end of the valve 100 to the transition portion 712. As shown in FIG. 8H, slit tube 704 can be a separate element that is adhered to (or otherwise coupled to) a widened section 714 of elongated shaft 708. Alternatively, slit tube 704 can be integral with the elongated shaft 708. Nose cone (nose piece) 802 provides a tapered surface for atraumatic tracking of the delivery assembly through the patient's vasculature. Nose cone 802 abuts cover 702 and can have a recessed portion so that cover 702 and nose cone 802 can combine to form a uniform outer surface.

In operation, once prosthesis assembly 114 is encapsulated in delivery system 700, the delivery system may be inserted into a body lumen, and stabilized at a target position. Next, moveable cover 702 may be slid back (proximally) relative to the prosthesis assembly 114. Once moveable cover 702 is slid back and the compressive forces of moveable cover 702 removed from slit tube 704, slit tube 704 and prosthesis assembly 114 can be easily repositioned relative to one another. Thus, slit tube 704 can be moved off of the prosthesis assembly 114 by pushing prosthesis assembly 114 forward (distally) or pulling slit tube 704 back (proximally), or both. Balloon member 112 can be inflated to deliver bioprosthesis 100 at the target position. After deployment of bioprosthesis 100, balloon member 112 can be deflated. Moveable cover 702 can be slid back (distally) over the deflated balloon member 112 and slit tube 704, and delivery system 700 can be retracted from the vasculature of the patient.

FIG. 9 is an illustration of yet another embodiment. In this embodiment a loading tool 1002 can assist the loading of prosthesis assembly 114 into the distal end of the delivery system 700 after the prosthesis assembly 114 is withdrawn from crimper 200. Loading tool 1002 can comprise a first section 1010 and a pushing member 1016. First section 1010 can have a hollow section with an internal diameter that varies from a larger diameter section 1012 to a smaller diameter section 1014. By positioning prosthesis assembly 114 into the larger diameter 1012 section and pulling or pushing prosthesis assembly 114 through the smaller diameter 1014 section of section 1010, the outer diameter (or radial profile) of prosthesis assembly 114 can be reduced.

Pushing member 1016 can have a handle portion 1017 and one or more extending members 1018 that extend from an end of pushing member 1016. In operation, prosthesis assembly 114 can be positioned at (or into) the larger diameter section 1012. Prosthesis assembly 114 can then be pushed further into first section 1010 until it reaches and passes through the smaller diameter section 1014. Prosthesis assembly 114 can be pushed (or urged) through the first section 1010 by extending members 1018, which can be configured to extend into the hollow section of first section 1010 and to contact a distal end of bioprosthesis 100.

Extending members 1018 can be formed in a variety of shapes. Extending members 1018 can be hollow (as shown in FIG. 10B) or solid. In addition, extending members 1018 can be formed with a number of slits that result in the extending member having a plurality of annularly spaced finger sections (as shown in FIG. 11B). Extending members can also be formed of a variety of materials. Desirably, extending members 1018 are configured so they can collapse to smaller outer diameter, in order to be able to push the prosthesis assembly 114 all the way into the smaller diameter section of the first section 1010. The extending members can be collapsible by forming the extending members with, for example, a flexible material, a plurality of slits, or both.

Desirably, extending members 1018 are sized and configured to follow the inner surface of hollow sections 1012 and 1014, so that extending members 1018 engage the prosthesis assembly 114 at its widest point. Because the implantable structure 102 of bioprosthesis 100 generally forms the widest area of the crimped prosthesis assembly 114, by forming extending members 1018 so they extend along the inner surface of the hollow sections (rather than through an inner area of the hollow section), the extending members 1018 can be configured to push against the implantable structure 102 (or frame), which is generally the most durable and tear resistant portion of bioprosthesis 100.

First section 1010 can also be attached to crimper 200 (as shown in FIG. 10) and prosthesis assembly 114 can be crimped to a small diameter and then the crimped prosthesis assembly 114 can be pulled back through the attached first section 1010 to further reduce the profile of the prosthesis assembly 114 or to maintain the desired crimped profile while transferring the prosthesis assembly 114 from the crimper 200 to the delivery device.

As shown in FIG. 10, first section 1010 can include be attached to crimper 200 to assist in loading prosthesis assembly 114 into delivery system 700. Prosthesis assembly 114 may be loaded into a slit tube 704 and cover 702 of a delivery system immediately after the prosthesis assembly 114 is crimped by crimper 200. Here, the distal end of the delivery system can be compressed by placing the distal end in the crimper jaws. Crimper 200 may be closed to a diameter that is smaller than the inner diameter of moveable cover 702, allowing prosthesis assembly 114 to be small enough in diameter to slide easily into moveable cover 702. By placing prosthesis assembly 114 into the larger diameter 1012 section and pulling or pushing prosthesis assembly 114 through the smaller diameter 1014 section of first section 1010, the outer diameter (or radial profile) of prosthesis assembly 114 can be reduced.

FIGS. 11A and 11B are illustrations of a loading tool 1102 with a first section 1010 and a pushing member 1016. In this embodiment, a tapered guide serves as an introduction channel into delivery system 700. Prosthesis assembly 114 can be pushed by a pushing member (slit tubular pusher) 1016 through tapered channel 1106 into moveable cover 702. Passing prosthesis assembly 114 through the tapered channel (hollow section) 1106 of Loading tool 1102 causes the prosthesis assembly 114 to have a reduced radial profile. Pushing member (slit tubular pusher) 1106 can be configured to be able to pass through both the larger diameter section 1012 and the smaller diameter section 1014, which allows the pushing member 1016 to be able to apply lateral pressure to prosthesis assembly 114 throughout the tapered channel 1106.

Loading tool 1102 can have a delivery system receiving area 1105, which is configured to receive a distal end of the delivery system. For example, moveable cover 702 can extend into the delivery system receiving area 1105 so that the prosthesis assembly 114 can be passed directly into the desired position on the delivery system after passing through the smaller diameter section 1014. In this manner, moveable cover 702 can be configured to compress around prosthesis assembly 114 as it is placed into moveable cover 702, thereby preventing the prosthesis assembly 114 from expanding (or recoiling) back to a larger diameter. A force F1 can be applied to the distal end of the delivery system to maintain the delivery system within the first section 1010 while the pushing member 1016 exerts a force F2 in the opposite direction. Desirably, a lip 1110 (shown in FIG. 11A) can be formed by a differential between the diameters of the delivery system receiving area 1105 and the smaller diameter section 1014. Lip 1110 is provided to abut the distal end of the delivery system when it is positioned in the delivery system receiving area 1105. The lip 1110 can help to maintain the delivery system in the desired position while loading the prosthesis assembly 114 through first section 1010. Slits can be provided on the pushing member 1016 to form fingers (extending members) 1108. The slits permit the fingers 1018 to contract to a smaller diameter, allowing fingers 1018 to more easily follow the inner surface of the tapered channel 1106 from the larger diameter section 1012 to the smaller diameter section 1014.

Figure 12:
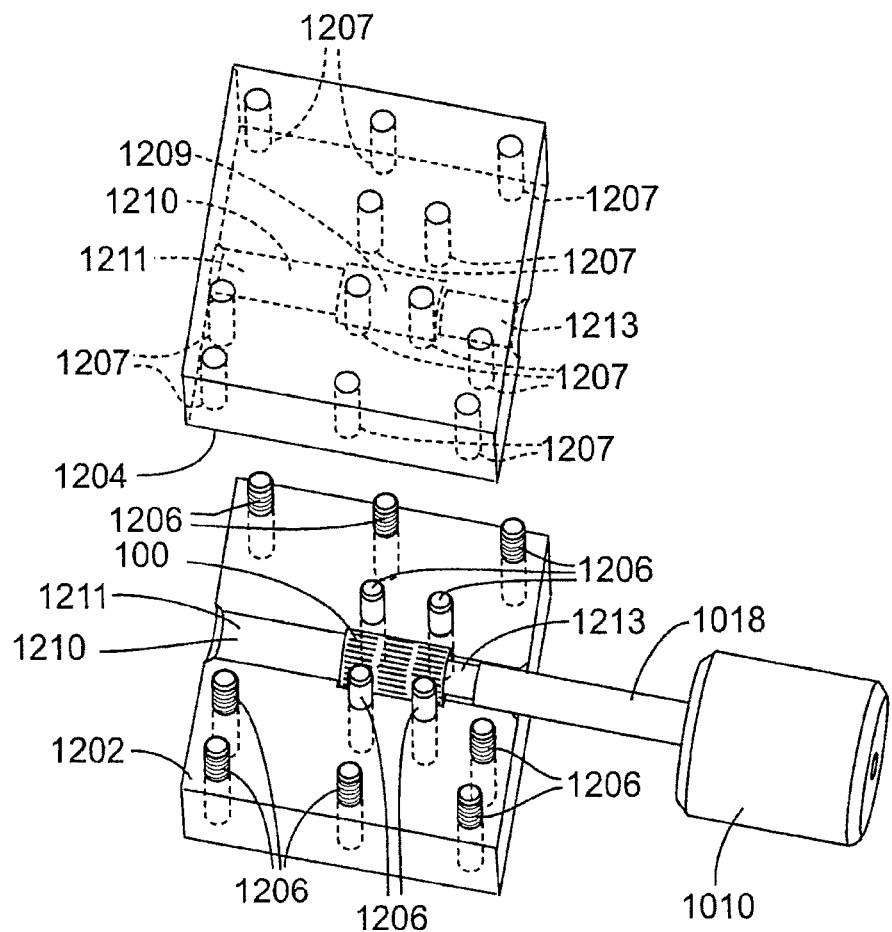
FIG. 12 is an illustration of a loading tool in accordance with an embodiment disclosed herein.

FIG. 12 is an illustration of a loading device that is configured to clamp prosthesis assembly 114 between two clamp portions 1202, 1204 to facilitate the loading of prosthesis assembly 114 into delivery system 700. Clamp portion 1202 has a plurality of pins 1206 that protrude from the surface of clamp portion 1202. Clamp portion 1204 has a plurality of openings 1207 that are configured to receive pins 1206. Channel 1210 can be formed by an opening on both clamp portions 1202, 1204 that extends from side of the loading device to the other. Channel 1210 can have a delivery system receiving area 1211, a prosthesis assembly receiving area 1209, and a pushing member receiving area 1213. FIG. 12 shows bioprosthesis 100 (without the balloon member for purposes of illustration) positioned in the prosthesis assembly receiving area 1209 of clamp portion 1202.

In this embodiment, prosthesis assembly 114 is positioned between four pins 1206 that protrude out of the clamp portion 1202 adjacent the prosthesis assembly receiving area 1209. A distal end of a delivery device can be positioned at one end of channel 1210, in the delivery system receiving area 1211. Clamp portion 1204 can then be positioned so that the openings 1207 mate with each of the protruding pins 1206 on face 1202 and the two faces can be pushed together. As clamp portion 1204 is pushed against clamp portion 1202, compressive forces urge prosthesis assembly 114 into a profile with a smaller diameter. Desirably, prosthesis assembly is urged into an oval shape. Prosthesis assembly 114 can then be pushed into an opening in a distal end of the delivery system, which has about the same diameter as the compressed prosthesis assembly 114. To push the prosthesis assembly 114 into the delivery system, a pushing member 1016 with extending members 1018 (such as those described above) can be pushed into the pushing member receiving area 1213 and up against the prosthesis assembly 114. By applying lateral pressure towards the delivery system with the pushing member, the prosthesis assembly 114 can be pushed into position within the distal end of the delivery system.

Channel 1210 can be formed in a variety of other configurations. For example, channel 1210 can be formed with one or more tapered sections so that the prosthesis assembly 114 can be reduced in diameter as it passes from a larger diameter section to a smaller diameter section (as discussed in more detail in other embodiments.) The number and orientation of pins and openings can also vary. For example, the loading device could have pins on both surfaces, and openings on both surfaces. Alternatively, another system besides pins could be used to align the two surfaces with one another.

The invention has been disclosed in an illustrative manner. Accordingly, the terminology employed throughout should be read in an exemplary rather than a limiting manner. Although minor modifications of the invention will occur to those of ordinary skill in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

We claim:

1. A method, the method comprising the steps of:
    providing an apparatus for reducing recoil of a prosthetic valve after it has been crimped on to a balloon member, the apparatus comprising:
        a prosthetic valve configured to be crimped from an expanded diameter to a crimped diameter, the prosthetic valve comprising a stent and a flexible membrane made of pericardium, the flexible membrane sutured to the stent and adapted for permitting blood flow in a first direction and substantially resisting flow in a second direction;
        a tube coupled to a distal section of an elongated shaft and adapted for covering the prosthetic valve, the tube having a first diameter in an uncompressed state and a second diameter in a compressed state, the tube having a distal end portion comprising one or more slits adapted to permit the distal end of the tube to flare outwardly in the uncompressed state for facilitating ejection of the prosthetic valve from the tube;
        a balloon catheter comprising a balloon member along a distal end portion, the balloon member having an external surface configured to receive the prosthetic valve in the crimped state, the balloon catheter advanceable through a lumen of the elongated shaft and tube;
        a compressing member adapted to compress the tube from the first diameter to the second diameter when the compressing member is advanced over the tube, the compressing member adapted for reducing recoil of the prosthetic valve after it has been crimped on to the balloon member; and
        a crimper suitable for radially crimping the prosthetic valve disposed within the distal end portion of the tube;
    crimping the prosthetic valve onto the balloon catheter using the crimper to provide a partially crimped prosthetic valve;
    advancing the distal end portion of the tube over the partially crimped prosthetic valve;
    crimping the partially crimped prosthetic valve and distal end portion of the tube using the crimper to provide the crimped prosthetic valve;
    advancing the compressing member over the distal end portion of the tube and crimped prosthetic valve;
    delivering the crimped prosthetic valve to a location within a native aortic valve of a patient while the crimped prosthetic valve is surrounded by the tube and compressing member;
    retracting the compressing member relative to the tube for allowing the distal end portion of the tube to flare outwardly;
    advancing the balloon catheter relative to the tube for advancing the crimped prosthetic valve out of the tube; and
    inflating the balloon member for expanding the crimped prosthetic valve within the native valve of the patient.

2. The method of claim 1, wherein the prosthetic valve radially expands to a recoil diameter after being crimped over the balloon member, the recoil diameter being smaller than the expanded diameter but larger than the crimped diameter, and wherein the compressing member has an inner diameter smaller than the recoil diameter for restricting radial expansion of the prosthetic valve after being crimped on to the balloon member.

3. The method of claim 1, wherein the tube is adhered to an inside portion of the distal section of the elongated shaft.

4. The method of claim 1, wherein the tube is integrally formed with the distal section of the elongated shaft.

5. The method of claim 1, wherein the distal section of the elongated shaft includes a distal end and the tube is coupled to the elongated shaft at an area just proximal to the distal end.

* * * * *